(12) United States Patent
Nagy et al.

(10) Patent No.: US 10,710,004 B2
(45) Date of Patent: Jul. 14, 2020

(54) WASTE STREAM UPGRADING IN A PROPYLENE OXIDE/STYRENE COPRODUCTION PROCESS

(71) Applicant: Lyondell Chemical Technology, L.P., Houston, TX (US)

(72) Inventors: Sandor Nagy, Seabrook, TX (US); Ha H. Nguyen, Houston, TX (US); Dan D. Lindsey, Houston, TX (US); Barbara Kimmich, Houston, TX (US); Nicholas Bruschi, Houston, TX (US); James D. Montano-Lawrence, Houston, TX (US); Justin E. Turner, Houston, TX (US); Debra L. Jackson, Houston, TX (US); Anthony S. Dearth, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 302 days.

(21) Appl. No.: 15/886,446

(22) Filed: Feb. 1, 2018

(65) Prior Publication Data
US 2018/0221787 A1    Aug. 9, 2018

Related U.S. Application Data

(60) Provisional application No. 62/454,542, filed on Feb. 3, 2017.

(51) Int. Cl.
| | |
|---|---|
| C07C 7/10 | (2006.01) |
| B01D 11/04 | (2006.01) |
| C07D 301/32 | (2006.01) |
| C07C 7/12 | (2006.01) |
| C07C 15/46 | (2006.01) |
| B01D 11/00 | (2006.01) |

(52) U.S. Cl.
CPC ...... B01D 11/0484 (2013.01); B01D 11/0492 (2013.01); C07C 7/10 (2013.01); C07C 7/12 (2013.01); C07C 15/46 (2013.01); C07D 301/32 (2013.01); B01D 2011/007 (2013.01)

(58) Field of Classification Search
CPC ...... B01D 17/042; B01D 17/047; B01J 23/40; B01J 21/18; B01J 23/42; B01J 23/44; B01J 35/0013; B01J 35/002; C07C 409/08; C07C 407/00; C07C 407/003; C07C 15/46
USPC .................................. 95/240 S; 210/600 S
See application file for complete search history.

(56) References Cited

U.S. PATENT DOCUMENTS

| | | | |
|---|---|---|---|
| 3,351,635 | A | 11/1967 | Chong |
| 3,439,001 | A | 4/1969 | Pell et al. |
| 4,066,706 | A | 1/1978 | Schmidt |
| 4,262,143 | A | 4/1981 | Becker |
| 5,210,354 | A | 5/1993 | Dubner et al. |
| 5,675,055 | A | 10/1997 | Evans et al. |
| 8,142,661 | B2 * | 3/2012 | Lindsey ............ C07C 7/10 203/39 |

FOREIGN PATENT DOCUMENTS

| | | |
|---|---|---|
| CN | 101323490 A | 12/2008 |
| EP | 767171 A1 | 4/1997 |
| GB | 647487 A | 12/1950 |

OTHER PUBLICATIONS

The International Search Report and Written Opinion for PCT/US2018/016465 dated Apr. 23, 2018.

* cited by examiner

Primary Examiner — Sharon Pregler

(57) ABSTRACT

A method including contacting an organic stream with water and carbon dioxide, whereby sodium is extracted from the organic stream, and separating an aqueous sodium salt-containing phase from an organic phase comprising a reduced sodium content. The organic stream can be a heavy residue formed in the co-production of propylene oxide and styrene. Contacting can include combining the carbon dioxide with the water to form a $CO_2$-saturated water stream and contacting the $CO_2$-saturated water stream with the organic stream, and/or combining the organic stream and the water to form a mixture and injecting the carbon dioxide as a gas thereinto. The method can further include repeating the contacting and the separating one or more times on the organic phase, subjecting the organic phase to ion exchange, or both, to obtain an organic phase having a further reduced sodium content. A system for carrying out the method is also provided.

18 Claims, 1 Drawing Sheet

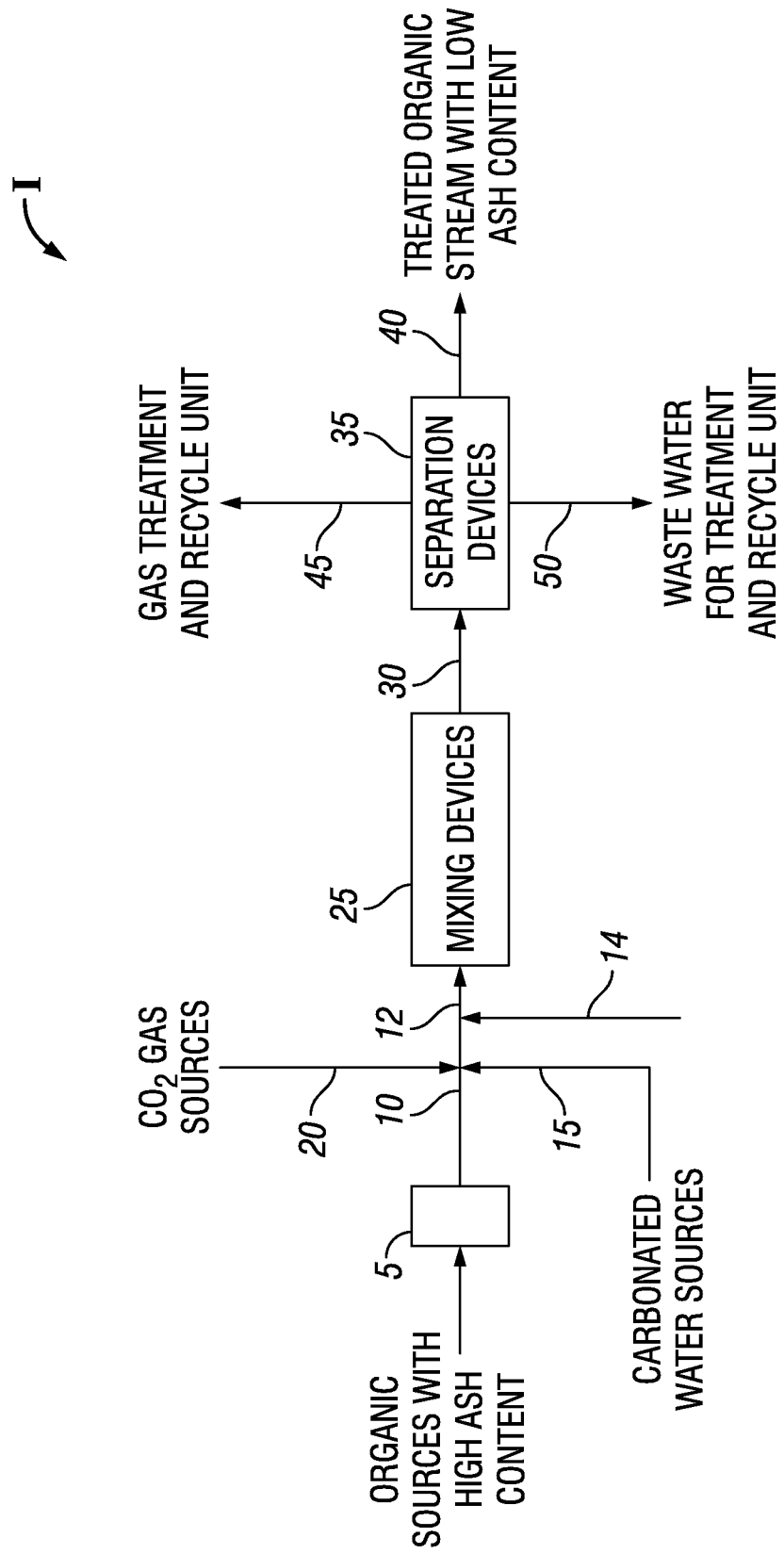

WASTE STREAM UPGRADING IN A PROPYLENE OXIDE/STYRENE COPRODUCTION PROCESS

CROSS-REFERENCE TO RELATED APPLICATIONS

This application claims the benefit of priority to U.S. Provisional Application No. 62/454,542 filed on Feb. 3, 2017, which is incorporated herein by reference in its entirety.

TECHNICAL FIELD

This disclosure relates to waste stream upgrading; more specifically, this disclosure relates to systems and methods for upgrading waste streams obtained during propylene oxide production; still more specifically, this disclosure relates to systems and methods for treating heavy residual process streams formed in the coproduction of propylene oxide and styrene monomer via contact of the residual process streams with carbon dioxide.

BACKGROUND OF THE INVENTION

The co-production of propylene oxide and styrene monomer, also known as the 'POSM' process, involves the oxidation of ethyl benzene to form ethyl benzene hydroperoxide, the catalytic reaction of the hydroperoxide with propylene to form propylene oxide and 1-phenyl ethanol, and the dehydration of the 1-phenyl ethanol to produce styrene monomer. In the POSM process, various distillation steps are employed in order to separate unreacted reagents, as well as various product streams, and one or more caustic treatment steps may be employed in order to reduce the acidic characteristics of various streams. In the process, a heavy residue stream containing relatively high levels of sodium compounds is formed. Without further treatment, the heavy residue stream is a low value product stream that may be useful only as a low grade fuel.

The low value product stream is conventionally treated with aqueous acid to form a mixture, and then phase separation of the resulting mixture provides an aqueous phase containing most of the sodium previously associated with the low value stream, and an organic phase having a reduced sodium content which can be used as higher grade fuel.

In conventional phase separation processes, it is often found that large volumes of a rag layer tend to form in the separator vessels. The rag layer is an emulsion of water in the heavy organic layer that does not separate into either an organic or an aqueous phase. The rag layer prevents complete separation of the aqueous and organic phases, and reduces the efficiency of the separation process.

Accordingly, an ongoing need exists for systems and methods for upgrading low value heavy residue(s) produced in the POSM process.

SUMMARY OF THE INVENTION

Herein disclosed is a method comprising: (a) contacting an organic stream with water and carbon dioxide, whereby sodium is extracted from the organic stream; and (b) separating an aqueous sodium salt-containing slurry phase from an organic phase comprising a reduced sodium content relative to the organic stream. In embodiments, the organic stream is a heavy residue formed in the co-production of propylene oxide and styrene. In embodiments, the contacting in (a) comprises combining the carbon dioxide with the water to form a $CO_2$-saturated water stream, and contacting the $CO_2$-saturated water stream with the organic stream. In embodiments, the contacting in (a) is performed co-currently, counter-currently, or a combination thereof. In embodiments, the method further comprises controlling the concentration of carbon dioxide in the $CO_2$-saturated water stream by controlling the temperature, the pressure, or both. In embodiments, the pressure is in the range of from about atmospheric pressure to about 500 psi, from about atmospheric pressure to about 100 psi, from about 10 psi to about 50 psi, or from about 20 psi to about 40 psi. In embodiments, the temperature is in the range of from about 5° C. to about 90° C., from about 15° C. to about 70° C., or from about 20° C. to about 60° C. In embodiments, the temperature is ambient temperature. In embodiments, the temperature is room temperature.

In embodiments, the contacting in (a) comprises combining the organic stream and the water to form a mixture, and injecting the carbon dioxide as a gas thereinto. In embodiments, injecting the carbon dioxide gas further comprises bubbling or sparging the carbon dioxide gas into the mixture. In embodiments, the carbon dioxide gas is injected at a flow rate in the range of from about 1 wt % to about 90 wt % of the combined mass of the organic and aqueous phases, from about 10 wt % to about 40 wt % of the combined mass of the organic and aqueous phases, or from about 10 wt % to about 25 wt % of the combined mass of the organic and aqueous phases. In embodiments, the contacting in (a) is performed at a pressure of greater than or equal to about atmospheric pressure. In embodiments, the separating in (b) further comprises separating a gas comprising carbon dioxide, a carrier gas, or both. In embodiments, the method further comprises recycling at least a portion of the separated gas to the contacting of (a). In embodiments, (a) and (b) are performed in a single apparatus.

In embodiments, the method further comprises: repeating (a) and (b) one or more times on the organic phase; subjecting the organic phase to ion exchange; or both, to obtain an organic phase having a further reduced sodium content. In embodiments, the method comprises subjecting the organic phase to ion exchange, wherein the ion exchange comprises cation exchange. In embodiments, the method comprises subjecting the organic phase to ion exchange, and the ion exchange is effected with an ion exchange resin comprising sulfonic acid groups. In embodiments, the method comprises subjecting the organic phase to ion exchange, and the ion exchange is effected with an ion exchange media that is natural or synthetic. In embodiments, the ion exchange is effected with an ion exchange resin selected from the group consisting of polymer resins, zeolites, clays, and combinations thereof.

In embodiments, the further reduced sodium content comprises a sodium content of less than about 100, 50, or 10 ppm sodium. In embodiments, the reduced sodium content comprises a sodium content of less than about 250, 150, or 100 ppm sodium. In embodiments, the organic stream and the water are present at a volumetric ratio in the range of from about 1:1 to about 10:1, from about 1:1 to about 8:1, or from about 1:1 to about 5:1. In embodiments, the contacting of (a), the separating of (b), or both are performed continuously. In embodiments, the separating of (b) is performed at a temperature in the range of from about 15° C. to about 85° C., from about 20° C. to about 70° C., or from about 30° C. to about 60° C.

The method may be carried out utilizing a two phase system or a three phase system. In embodiments, the carbon dioxide is provided by a gas selected from the group consisting of pure carbon dioxide, other gases comprising greater than about 50 volume percent carbon dioxide, and combinations thereof. In embodiments, the gas comprising greater than about 50 volume percent carbon dioxide is a flue gas. In embodiments, the flue gas comprises greater than about 70 volume percent carbon dioxide. In embodiments, at least a portion of the contacting of (a) occurs in a liquid-liquid contactor. In embodiments, the liquid-liquid contactor is selected from the group consisting of mixer-decanters, liquid-liquid extractors, mixer-separator devices, and combinations thereof.

Also disclosed herein is a method comprising: (a) contacting a mixture comprising an organic stream and water with carbon dioxide gas, and (b) separating an aqueous sodium salt-containing phase from an organic phase comprising a reduced sodium content relative to the organic stream, wherein the organic stream is a heavy residue formed in the co-production of propylene oxide and styrene.

Also disclosed herein is a method comprising: (a) contacting an organic stream with a $CO_2$-saturated water stream, and (b) separating an aqueous sodium salt-containing phase from an organic phase comprising a reduced sodium content relative to the organic stream, wherein the organic stream is a heavy residue formed in the co-production of propylene oxide and styrene.

Also disclosed herein is a system comprising: (a) a mixing device configured for contacting an organic stream with water and carbon dioxide, whereby sodium is extracted from the organic stream, wherein the organic stream is a heavy residue formed in the co-production of propylene oxide and styrene; (b) a separation device configured for separating an aqueous sodium salt-containing phase from an organic phase comprising a reduced sodium content relative to the organic stream; and (c) a POSM system configured to produce polypropylene and styrene monomer, and from which the organic stream is generated.

Also disclosed herein is a method comprising: (a) recovering a heavy organic stream comprising sodium from a propylene oxide and styrene monomer co-production (POSM) process; (b) contacting the organic stream with water and carbon dioxide, whereby sodium is the organic stream; and (c) separating an aqueous sodium salt-containing slurry phase from an organic phase comprising a reduced sodium content relative to the organic stream, wherein the POSM process comprises oxidation of ethyl benzene to form ethyl benzene hydroperoxide, catalytic reaction of the hydroperoxide with propylene to form propylene oxide and 1-phenyl ethanol, and dehydration of the 1-phenyl ethanol to produce styrene monomer. In embodiments, the heavy organic stream comprising sodium is a waste or by-product stream comprising ash recovered from a POSM process. In embodiments, the waste or by-product stream comprising ash is recovered from one or more distillation and/or caustic treatment steps in a POSM process.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the detailed description hereinbelow is to be regarded as illustrative in nature and not restrictive.

BRIEF DESCRIPTION OF THE DRAWING

The following FIGURE illustrates an embodiment of the subject matter disclosed herein. The claimed subject matter may be understood by reference to the following description taken in conjunction with the accompanying FIGURE, in which like reference numerals identify like elements, and in which:

The FIGURE is a schematic of a system for carrying out upgrading of a POSM waste stream according to an embodiment of this disclosure.

DETAILED DESCRIPTION

Herein disclosed are systems and methods for upgrading waste streams generated in a propylene oxide/styrene process. As noted hereinabove, large volumes of waste streams contaminated by ash (primarily sodium), and useful only as a low quality fuel, are produced during processes, such as the POSM process. De-ashing (e.g., removal of at least a portion of the sodium content thereof) can be effected to increase the fuel quality of such waste streams. It has been unexpectedly discovered that de-ashing of a waste stream generated in a propylene oxide/styrene process can be effected via the herein-disclosed treatment system and method, to provide a stable, low sodium, and neutral organic phase. Treatment is effected via the utilization of carbon dioxide as the de-ashing agent. The resulting de-ashed organic phase can be utilized as a higher quality, stable fuel, and/or can be further upgraded to capture the chemical value thereof.

Although referred to as a 'waste' stream, it is to be understood that a POSM 'waste' stream de-ashed via the present disclosure may be utilizable as a fuel, and the term 'waste' indicates that the stream is not a main value product of a POSM process, but a by-product thereof. Furthermore, although description of the herein-disclosed method and system are provided with reference to de-ashing of a POSM waste stream, the herein-disclosed system and method may be suitable for de-ashing of organic streams produced in processes other than POSM processes.

As noted hereinabove, conventional processes for removing sodium from waste streams produced in POSM processes often utilize one or more caustic treatment steps. Some processes involve mixing of the propylene oxide/styrene waste stream with a hydrocarbon and an aqueous acid, and subsequent separation of the mixture into an aqueous sodium salt-containing slurry phase and an organic phase reduced in sodium, which may be utilized for fuel applications. While such processes may be efficient in reducing the sodium contamination in the waste stream(s), they can undesirably generate a large volume of acidic waste stream(s), and can result in a fuel product that is acidic, potentially resulting in corrosion and susceptibility to undesired decomposition/fouling.

According to this disclosure, carbon dioxide, rather than or in addition to a mineral acid such as sulfuric acid, is utilized as a convenient agent to treat an 'organic stream' (which may, in embodiments, be a POSM waste stream, or a POSM waste stream diluted as described further hereinbelow). Without limitation, the carbon dioxide can be combined in an aqueous phase prior to contacting with the organic waste stream, or the carbon dioxide can be combined with a mixture of the organic waste stream and water. In embodiments, the herein-disclosed carbon dioxide treatment replaces conventional mineral acid treatment. In other embodiments, carbon dioxide treatment according to this disclosure is utilized in combination with (e.g., subsequent to) conventional mineral acid treatment.

Herein disclosed is a system for upgrading a waste stream produced during the co-production of propylene oxide and styrene monomer. A system for upgrading a waste stream produced during a POSM process will now be described with reference to the FIGURE, which is a schematic of a system I for carrying out upgrading of a POSM waste stream according to an embodiment of this disclosure. System I comprises a source of a stream having an ash (e.g., sodium) content to be reduced 5, one or more mixing devices 25, and one or more separation devices 35. Although depicted as separate devices in the embodiment of the FIGURE, mixing device 25 and separation device 35 may be provided in a single mixer/separator device, in some embodiments. A line 10 may fluidly connect (or comprise) the source of the stream having the ash content to be reduced 5 with the one or more mixing devices 25. One or more lines 20 may be configured to introduce carbon dioxide gas from a carbon dioxide gas source into line 10. Alternatively or additionally, a line 20 may be configured to introduce carbon dioxide gas from a carbon dioxide gas source directly into mixing device 25. One or more lines 15 may be configured to introduce carbonated water from a carbonated water source into organic phase inlet line 10. Alternatively or additionally, a line 15 may be configured to introduce carbonated water from a carbonated water source directly into mixing device 25. A line 14 may be configured for the introduction of water ('aqueous phase') into organic phase inlet line 10, whereby a mixture of water and organic phase can be introduced into mixing device 25 via combined mixer inlet line 12. Alternatively or additionally, a water inlet line 14 may be configured to introduce water directly into mixing device 25.

A line 30 may fluidly connect mixing device 25 with separation device 35, whereby a mixture produced via the combination of the organic waste stream, water, and carbon dioxide in mixing device 25 can be introduced into separation device 35. A gas outlet line 45 may be fluidly connected with separation device(s) 35, and configured for the removal of gas (e.g., carbon dioxide) from separation device(s) 35. Gas outlet line 45 may fluidly connect separation device 35 with a gas treatment and recycle unit configured to treat and/or recycle a gas, for example carbon dioxide, to mixing device(s) 25. In embodiments, the system may comprise a compressor configured to compress the carbon dioxide and/or other recycled gas for introduction into mixing device 25. An organic phase outlet line 40 may be fluidly connected with separation device(s) 35, and configured for the removal from separation device(s) 35 of a treated organic stream having a reduced ash content in comparison to the ash content of the source stream 5. An aqueous phase outlet line 50 may be fluidly connected with separation device(s) 35, and configured for the removal of an ash-enriched aqueous phase therefrom. Aqueous phase outlet line 50 may fluidly connect separation device(s) 35 with a waste water treatment and/or recycle unit configured to treat and/or recycle water, for example, to mixing device(s) 25.

System I may be operable as a two phase system or a three phase system. In embodiments, the system is operable with an organic phase and an aqueous phase. In embodiments, there is also a gas phase.

Also disclosed herein is a method of reducing ash (e.g., sodium) content in a heavy residue, such as that formed in a POSM process for the co-production of propylene oxide and styrene. The method comprises: (a) contacting an organic stream with water and carbon dioxide, whereby sodium is extracted from the organic stream; and (b) separating an aqueous sodium salt-containing slurry phase from an organic phase comprising a reduced sodium content relative to the organic stream. In embodiments, the organic stream is a heavy residue formed in the co-production of propylene oxide and styrene. Such a method will now be described with reference to the FIGURE, which is a schematic of a system for carrying out upgrading of a POSM waste stream according to an embodiment of this disclosure. A POSM waste stream to be treated is introduced from POSM waste stream source 5 into mixing device 25 via organic phase inlet line 10. The POSM waste stream can be produced via any POSM process known to those of skill in the art to provide an ash-containing (e.g., sodium-containing) waste stream.

The organic stream with 'high' ash content to be de-ashed can comprise from about 500 ppm to about 10,000 ppm ash, from about 700 ppm to about 10,000 ppm ash, or from about 1000 ppm to about 5000 ppm ash. In embodiments, the ash comprises greater than or equal to about 97%, 98%, or 99% sodium. The ash may further comprise minor amounts of other metals, such as, without limitation, Fe, Mg, Ca, and K. The organic stream with 'high' ash content to be de-ashed can comprise from about 500 ppm to about 10,000 ppm sodium, from about 700 ppm to about 10,000 ppm sodium, or from about 1000 ppm to about 5000 ppm sodium. In embodiments, the organic stream to be de-ashed comprises greater than or equal to about 500, 750, 1000, 2500, 3000, 4000, 5000, 6000, 7000, 8000, 9000, or 10,000 ppm sodium.

In embodiments, the organic stream is modified with a different organic material or a mixture of organic materials to achieve a desirable viscosity and/or density, to enhance the separation between the organic phase and the aqueous phase. In embodiments, the viscosity of the organic phase is less than 20 cP, less than 10 cP, or less than 2 cP. In embodiments, the density of the organic phase is less than 1.0 g/cc, less than 0.975 g/cc, or less than 0.95 g/cc.

In embodiments, the heavies residue of a POSM process is diluted via combination with one or more other organic chemicals, such as, without limitation, those comprising aliphatic or aromatic groups, to form the organic stream prior to contact with carbon dioxide. In embodiments, the one or more other organic chemicals comprise ethyl benzene, toluene, cumene, xylene, hexane, heptane, octane, nonane, decane, etc., or a combination thereof. In embodiments, the heavies residue is combined with ethyl benzene prior to contact of the organic stream with carbon dioxide. In embodiments, the weight ratio between the heavies residue and the one or more other organic chemicals (e.g., ethyl benzene) is in the range of from about 1:10 wt/wt ratio to about 2:1 wt/wt ratio, from about 1:10 wt/wt ratio to about 1:1 wt/wt ratio, or from about 1:8 wt/wt ratio to about 2:1 wt/wt ratio.

According to the herein-disclosed method, the organic stream is contacted with carbon dioxide. In embodiments, the organic phase to be de-ashed is thoroughly mixed with the carbon dioxide and water (and/or carbonated water) prior to the separation step. The carbon dioxide and water may be added simultaneously (e.g., as carbonated water), or can be added separately to the organic phase. The order of addition of the carbon dioxide and water may not be critical. In embodiments, the contacting is accomplished at relatively mild conditions. Contacting conditions can comprise a temperature in the range of from 20° C. to 100° C., from 40° C. to 90° C., from 5° C. to 90° C., from 15° C. to 70° C., or from 20° C. to 60° C. The contacting of the organic waste stream with carbon dioxide may be performed at ambient or above ambient pressure. While the contacting may be effective at ambient temperature, efficiency of sodium removal may be maintained or even increased at temperatures above or below ambient temperature. In embodiments, contacting and separation are performed in a single vessel, and the carbon dioxide, water, and/or carbonated water is added directly into the separation vessel along with the organic phase to be de-ashed.

In embodiments, contacting comprises combining the carbon dioxide with water to form a $CO_2$-saturated water stream, and contacting the $CO_2$-saturated water stream with the organic stream. For example, in embodiments, carbonated water is formed via contacting carbon dioxide gas with water to produce a carbonated water source or stream, which is combined with the POSM waste stream in line 10 via introduction thereto via carbonated water line 15. In embodiments, carbonated water in carbonated water line 15 and POSM waste introduced via organic phase inlet line 10 can be introduced into mixing device 25 via combined mixer inlet line 12. In alternative embodiments, organic phase to be de-ashed and carbonated water are introduced separately, via organic phase inlet line 10 and carbonated water inlet line 15 into mixing device 25.

In embodiments, the organic phase comprising POSM waste to be de-ashed and water are present within mixing device 25 at a volumetric ratio in the range of from about 1:1 to about 10:1, from about 1:1 to about 8:1, or from about 1:1 to about 5:1.

In embodiments, the carbonated water stream introduced into mixing device 25 via carbonated water inlet line 15 comprises a carbon-dioxide saturated water stream. The concentration of carbon dioxide in the $CO_2$-saturated water stream can be controlled, in embodiments, by controlling the temperature, the pressure, or both. The pressure can be in the range of from about atmospheric pressure to about 500 psi, from about atmospheric to about 100 psi, from about 10 psi to about 50 psi, or from about 20 psi to about 40 psi. The temperature can be in the range of from about 5° C. to about 90° C., from about 15° C. to about 70° C., or from about 20° C. to about 60° C. In embodiments, the temperature is ambient temperature. In embodiments, the temperature is room temperature. In embodiments, a temperature below room temperature, a higher pressure, or both, is utilized to increase the amount of carbon dioxide in the $CO_2$-saturated water stream. The contacting of the carbonated water stream and the organic phase can be performed co-currently or counter-currently.

Mixing device 25 can comprise a liquid-liquid contactor, in which carbonated water (introduced via carbonated water inlet line 15 and mixing device inlet line 12, or introduced directly into mixing device 25) is contacted with the organic phase (introduced thereto via organic phase inlet line 10 and mixing device inlet line 12, or introduced directly into mixing device 25). Liquid-liquid contactors include, without limitation, mixer-decanters, liquid-liquid extractors, mixer-separator devices, and combinations thereof.

In embodiments, the method comprises combining the organic stream and water (or 'aqueous phase') to form a mixture, and injecting the carbon dioxide as a gas thereinto. For example, in embodiments the organic phase is combined with water, and carbon dioxide gas is introduced thereinto, for example via carbon dioxide inlet line 20. In embodiments, water is combined, for example via water inlet line 14, with the organic phase in organic phase inlet line 10 to provide a mixture of the organic phase and water which is introduced into mixing device 25 via mixing device inlet line 12. In embodiments, water is introduced into mixing device inlet line 12 via a water inlet line 14. In embodiments, water is introduced directly into mixing device 25.

The carbon dioxide can be provided by a gas selected from the group consisting of pure carbon dioxide and/or other gases comprising greater than about 50 volume percent carbon dioxide. In embodiments, the gas comprising greater than about 50 volume percent carbon dioxide is a flue gas. The flue gas can comprise greater than about 70 volume percent carbon dioxide. In embodiments, the carbon dioxide is provided by a gas comprising greater than 80, 85, 90, 95, 96, 97, 98, or 99 volume percent carbon dioxide.

The carbon dioxide gas can be bubbled, sparged, or otherwise introduced into a mixture comprising the organic phase and water. For example, mixing device 25 may comprise a sparger, through which carbon dioxide gas bubbles are introduced into a mixture of the organic and aqueous phases. In embodiments, the carbon dioxide gas is injected at a flow rate that provides from about 1 wt % to about 90 wt % of the combined mass of the organic and aqueous phases, from about 10 wt % to about 40 wt % of the combined mass of the organic and aqueous phases, or from about 10 wt % to about 25 wt % of the combined mass of the organic and aqueous phases. The carbon dioxide gas may be contacted with the organic and aqueous phases at a pressure of greater than or equal to about atmospheric pressure.

Following contacting of the organic phase with carbon dioxide as described hereinabove, the resulting mixture is separated into immiscible phases, via separation device 35. Sodium salts and ash may be solubilized in the aqueous phase. Specifically, separation provides an aqueous sodium-containing phase and an organic phase having reduced sodium content relative to the organic stream, wherein the reduced sodium content is below that expected from water addition or dilution alone. In embodiments such as shown in the FIGURE, after contacting of the organic phase with water and carbon dioxide (either via contact of the organic phase with carbonated water, via contacting of carbon dioxide gas with a mixture of the organic phase and water, or both) in mixing device 25, the mixture is introduced into one or more separation devices 35. As indicated in the FIGURE, a mixture outlet line 30 may introduce the mixture resulting from the contacting into separation device 35. As noted hereinabove, in embodiments, separation device 35 may be a separation zone within mixing device 25, or may be the same vessel. That is, contacting/mixing of the carbon dioxide with the organic phase, and separation of the organic phase from an aqueous phase may occur within a single apparatus or device, in embodiments. The separation is operated under conditions that provide an immiscible aqueous sodium-containing phase and an organic phase having reduced sodium content.

Separation device 35 is operable to separate an organic phase having reduced sodium content (i.e., a de-ashed organic phase) from an aqueous phase containing extracted ash (e.g., sodium). A treated organic stream having a lower/reduced ash content may be extracted from separation device 35 via upgraded or 'treated' POSM waste line 40. An aqueous phase comprising increased ash is extracted from separation device 35 via aqueous phase outlet line 50. The aqueous phase can be sent for waste water treatment, recycled, or the like, as known to those of skill in the art. The phase separation temperature can vary depending on operating conditions such as the pressure. In embodiments, separation may be performed at a temperature in the range of from about 15° C. to about 85° C., from about 20° C. to about 85° C., from about 20° C. to about 70° C., from about 25° C. to about 70° C., or from about 30° C. to about 60° C. In embodiments, the phase separation is performed at a higher temperature than the contacting/mixing. Utilization of a higher phase separation temperature may enhance the separation of carbon dioxide gas from the organic and aqueous phases, in embodiments.

The treated, 'reduced ash' organic phase can comprise a sodium content of less than about 250, 150, or 100 ppm sodium. In embodiments, the 'reduced' sodium content comprises a sodium content that is at least 50, 60, or 75% less than the sodium content expected from simply contacting the organic phase to be de-ashed with an equivalent amount of water (i.e., via the same method absent the carbon dioxide). In embodiments, the de-ashed organic phase comprises a sodium content that is less than 90, 92.5, or 95% that of the organic phase prior to treatment. The treated, 'reduced ash' organic phase can comprise an ash content of less than about 250, 150, or 100 ppm ash. In embodiments, the 'reduced' ash content comprises an ash content that is at least 50, 60, or 75% less than the ash content expected from simply contacting the organic phase to be de-ashed with an equivalent amount of water (i.e., via the same method absent the carbon dioxide). In embodiments, the de-ashed organic phase comprises an ash content that is less than 90, 92.5, or 95% that of the organic phase prior to treatment.

In embodiments, the separation is effected via different gravity-driven methods, such as, without limitation, gravity separation via decantation, or via forced methods of enhancing separation, such as, without limitation, via centrifugation, or via combination thereof, such as, without limitation, via a coalescer. In embodiments, certain chemicals, such as de-emulsifiers, which can enhance the separation, are employed in conjunction with the separation operations.

In embodiments, the separation is performed by gravity-driven phase separation, such as decantation. In decantation, the mixed aqueous/carbon dioxide/residue stream in mixture outlet line 30 can be introduced into a decanter unit separation device 50, where phase separation takes place. In embodiments, gravity driven phase separation can provide an aqueous sodium salt-containing phase and an organic phase having reduced sodium content. For decantation, the volume of the decanter should provide a residence time adequate for phase separation to occur at a specified flow rate.

In embodiments, a combined mixing/separation vessel is periodically mixed or agitated, and then agitation is ceased, and the phases allowed to separate for a time. For example, a mixture of the aqueous and organic phases may be periodically sparged with carbon dioxide gas, or a mixture of carbonated water and organic phase can be periodically agitated (example, via a stirrer, via circulation around a circulation loop, or other means). The phases may then be allowed to separate for a time period of, for example, 1, 2, 3, or 4 hours, or more, up to 1 or 2 days or more, until phase separation is effected. Once separation is effected, the aqueous layer can be drained, leaving a neutral organic phase, which has been de-ashed. Alternatively, the upgraded organic phase (top layer reduced in sodium) can be extracted or decanted from the top of the vessel, leaving the sodium-enhanced aqueous (bottom) layer.

In embodiments, the method further comprises separating a gas comprising carbon dioxide, a carrier gas (e.g., an inert gas such as nitrogen), or both. For example, a gas outlet line 45 may be operable to extract a gas from separation device 35. Separated gas may be treated and/or recycled. For example, carbon dioxide gas extracted from separation device 35 can, in embodiments, be recycled to mixing device 25.

The method can further comprise repeating the contacting of the organic phase with carbon dioxide, the separation of the aqueous phase from the organic phase, or both the contacting and the separating steps one or more times to obtain an organic phase having a further reduced ash and/or sodium content. For example, treated organic phase extracted from separation device 35 via upgraded POSM waste stream outlet line 40 may be recycled to mixing device 25, for example, via organic phase inlet line 10.

In embodiments, the method further comprises subjecting the organic phase to one or more ion exchange 'polishing' steps to further reduce the ash and/or sodium content of the organic phase. Subjecting the organic phase to ion exchange, may comprise subjecting the organic phase to cation exchange. Ion exchange may be effected via any ion exchange known to those of skill in the art. For example, in embodiments, ion exchange is effected with an ion exchange resin comprising sulfonic acid groups. The ion exchange may be carried out utilizing an ion exchange media that is natural or synthetic. In embodiments, the ion exchange is effected with an ion exchange resin selected from the group consisting of polymer resins, zeolites, clays, and combinations thereof. For example, the acidic form of zeolites and/or layered materials, such as clays, may provide effective ion exchange media, in embodiments.

The organic phase having a 'further reduced' ash content can comprise an ash content of less than about 100, 50, or 10 ppm ash. In embodiments, the 'further reduced' ash content comprises an ash content that is at least 50, 60, or 75% less than the ash content expected from simply contacting the organic phase to be de-ashed with an equivalent amount of water. In embodiments, the further de-ashed organic phase comprises an ash content that is less than 95, 97.5, or 99.0% that of the organic phase prior to treatment. In embodiments, the organic phase having a 'further reduced' sodium content can comprise a sodium content of less than about 100, 50, 10, or 1 ppm sodium. In embodiments, the 'further reduced' sodium content comprises a sodium content that is at least at least 50, 60, or 75% less than the sodium content expected from simply contacting the organic phase to be de-ashed with an equivalent amount of water. In embodiments, the 'further reduced' sodium content comprises a sodium content that is less than 95, 97.5, or 99.0% that of the organic phase prior to treatment.

In embodiments, the method is performed continuously. In embodiments, the contacting of the organic stream to be treated/de-ashed, the separating of the reduced ash organic phase from the increased ash aqueous phase, or both is performed continuously.

In embodiments, the de-ashed organic phase having reduced ash content (and comprising heavy organic components formed in the POSM process) is utilized as an upgraded fuel stream without further processing. In embodiments, the organic phase having reduced sodium content is further processed.

Optional Further Processing of De-Ashed Organic Phase

In embodiments, at least a portion of the de-ashed organic phase having reduced sodium content is further upgraded by cracking to produce styrene monomer. In such embodiments, a compatible acid catalyst, such as, without limitation, p-toluene sulfonic acid can be added to the organic phase, and the resulting mixture cracked at elevated temperature to form 1-phenyl ethanol and styrene monomer. In embodiments, the 1-phenyl ethanol and styrene monomer are separated by distillation from remaining heavy materials. Conditions for the cracking are known in the art, and include, without limitation, temperatures in the range of from 70° C. to 300° C., from 120° C. to 220° C., or from 70° C. to 220° C., and pressures below atmospheric, e.g., 100 mm Hg (1.9 psi) to 400 mm Hg (7.7 psi), which are appropriate for vaporization of light materials.

In embodiments, at least a portion of the de-ashed organic phase is subjected to a wiped film evaporation in order to separate a portion of the stream as a volatile overhead fraction. In embodiments, this overhead fraction is cracked at elevated temperatures (as described above) to produce styrene monomer. In embodiments, the volatile overhead stream is passed directly to the 1-phenyl ethanol dehydration step employed in the POSM process from which the POSM waste to be de-ashed was generated, whereby components of the volatile overhead are converted to styrene monomer at the conditions employed for the 1-phenyl ethanol dehydration.

Product 1-phenyl ethanol and styrene monomer from the optional further processing of the de-ashed organic phase can represent increased yields of desired products obtainable via an overall POSM process. Furthermore, the heavy materials from the optional upgrade/further processing can be useful as an upgraded fuel by virtue of the low sodium content thereof.

Production of POSM Waste Stream to be De-Ashed

In embodiments, the method further comprises generating, via a POSM process, a POSM waste stream to be upgraded/de-ashed according to the herein-disclosed system and method. POSM processes are well known in the art, and a waste stream treated via the system and method of this disclosure can be produced via any known POSM process. For example, POSM processes are described in U.S. Pat. Nos. 3,351,635; 3,439,001; 4,066,706; 4,262,143; and 5,210,354, the disclosure of each of which is hereby incorporated herein in its entirety for all purposes not contrary to this disclosure.

In embodiments of the POSM process via which the POSM waste stream to be de-ashed is generated, ethyl benzene is reacted with molecular oxygen at elevated temperature, in accordance with known techniques, to form ethyl benzene hydroperoxide. A small amount of alkali may be incorporated in the oxidation mixture in order to improve oxidation rate and selectivity. In embodiments, the ethyl benzene hydroperoxide is subsequently reacted with propylene to form propylene oxide and 1-phenyl ethanol. The epoxidation reaction mixture may be caustic washed and subjected to a series of distillations in order to separate materials contained therein. In embodiments, the reaction mixture is distilled to separate unreacted propylene overhead from heavier components. The separated propylene may be recycled to the epoxidation step. In embodiments, the heavier components are further distilled, optionally after caustic wash, in a series of distillations to separate product propylene oxide, product 1-phenyl ethanol, and unreacted ethyl benzene, which can be recycled, optionally after a caustic wash. The 1-phenyl ethanol stream can be dehydrated to product styrene monomer. In embodiments, a heavy organic sodium containing low value product stream resulting from such separation processes, or the like, is utilized as the POSM waste stream introduced into mixing device 25 via organic phase inlet line 10, whereby the sodium-containing heavy residue can be treated as described hereinabove in order to upgrade (e.g., de-ash) the stream.

In embodiments, the heavy organic residue stream from the propylene oxide/styrene monomer process comprises primarily oxygenated aryl compounds, which may have, without limitation, molecular weights greater than or equal to 90 g/mol, 94 g/mol, 200 g/mol, 215 g/mol, or 225 g/mol. In embodiments, the heavy organic residue stream from the propylene oxide/styrene monomer process comprises oxygenated aryl compounds. In embodiments, the heavy organic residue stream from the propylene oxide/styrene monomer process comprises primarily oxygenated aryl compounds. In embodiments, the heavy organic residue stream from the propylene oxide/styrene monomer process comprises at least 20, 30, 40, or 50 weight percent oxygenated aryl compounds. In embodiments, the organic stream to be de-ashed comprises greater than or equal to about 0.25 wt % (2,500 ppm), 0.3 wt % (3,000 ppm), 0.4 wt % (4,000 ppm), 0.5 wt % (5,000 ppm), 0.75 wt % (7,500 ppm), or 1.0 wt % (10,000 ppm) ash. The ash may comprise primarily sodium. In embodiments, the organic stream to be de-ashed comprises greater than or equal to about 0.25 wt % (2,500 ppm), 0.3 wt % (3,000 ppm), 0.4 wt % (4,000 ppm), 0.5 wt % (5,000 ppm), 0.75 wt % (7,500 ppm), or 1.0 wt % (10,000 ppm) sodium.

The system and method of this disclosure provide for removal of ash from a heavy residue, such as that formed in the co-production of propylene oxide and styrene. The process of the disclosure comprises contacting the heavy residue with carbon dioxide and water, and separating the resulting mixture into an aqueous sodium salt containing phase and an organic phase having reduced sodium content. The disclosed system and method enable enhanced removal of sodium from the organic phase relative to systems and methods absent the carbon dioxide, and enable sodium removal without or with a reduced usage of the conventional utilization of acid and/or added solvent to control the properties of the organic stream.

The following examples merely illustrate the system and method of this disclosure. Those skilled in the art will recognize many variations that are within the spirit of this disclosure and the scope of the claims.

EXAMPLES

Example 1

Single Treatment of Organic Waste Stream According to this Disclosure

Experiments were performed to study the effectiveness of waste water stream treatment according to this disclosure. In this example, 2 liters of a basic propylene oxide/styrene process waste stream containing about 4000 ppm of sodium was diluted with 2 liters of ethyl benzene (resulting in about 2000 ppm sodium in the organic phase), and combined with four liters of water. The process waste stream comprised a mixture of methyl benzyl alcohol, 2-phenyl ethanol, and ethers thereof, and included higher molecular weight components. The diluted mixture was combined in a 5 gallon vessel equipped with a recirculation loop and a dip-tube for carbon dioxide purging. The vessel was then purged with carbon dioxide, and pressurized up to 30 psi of carbon dioxide pressure. The mixture was periodically (three times, at an interval of one hour) mixed by circulating the liquid through the recirculation loop for approximately one minute. After four hours, the mixture was allowed to separate for four hours, and the aqueous layer was drained from the vessel, providing a neutral, organic phase containing about 250 ppm of sodium. This Example illustrates that a single treatment according to this disclosure can provide significant sodium reduction, in this case from about 4000 ppm to about 250 ppm.

Example 2

Dual Treatment of Organic Waste Stream According to this Disclosure

The organic phase resulting from Example 1, containing about 250 ppm of sodium, was again treated according to this disclosure, by mixing with fresh water and carbon dioxide as per Example 1. The treatment resulted in an organic phase containing less than about 10 ppm sodium. This Example illustrates that a secondary treatment provided further reduction in sodium level, in this case from about 250 ppm sodium to less than about 10 ppm sodium.

Example 3

Three Step Treatment of Organic Waste Stream According to this Disclosure

The two liters of the organic phase from Example 1, containing about 250 ppm of sodium was treated via flow through a bed containing 4 grams of LEWATIT® K2629 ion exchange resin (available from LANXESS Chemical Company in Shanghai, China) at the rate of 0.25 mL/min. The resulting effluent organic phase contained less than 1 ppm sodium. This Example illustrates that the sodium was further reduced by passing the treated feed through an ion exchange resin in acidic form to produce an organic phase with a sodium content of less than about 1 ppm.

ADDITIONAL DISCLOSURE

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method comprising: (a) contacting an organic stream with water and carbon dioxide, whereby sodium is extracted from the organic stream; and (b) separating an aqueous sodium salt-containing slurry phase from an organic phase comprising a reduced sodium content relative to the organic stream.

B: A method comprising: (a) contacting a mixture comprising an organic stream and water with carbon dioxide gas; and (b) separating an aqueous sodium salt-containing phase from an organic phase comprising a reduced sodium content relative to the organic stream, wherein the organic stream is a heavy residue formed in the co-production of propylene oxide and styrene.

C: A method comprising: (a) contacting an organic stream with a $CO_2$-saturated water stream; and (b) separating an aqueous sodium salt-containing phase from an organic phase comprising a reduced sodium content relative to the organic stream, wherein the organic stream is a heavy residue formed in the co-production of propylene oxide and styrene.

D: A system comprising: (a) a mixing device configured for contacting an organic stream with water and carbon dioxide, whereby sodium is extracted from the organic stream, wherein the organic stream is a heavy residue formed in the co-production of propylene oxide and styrene; (b) a separation device configured for separating an aqueous sodium salt-containing phase from an organic phase comprising a reduced sodium content relative to the organic stream; and (c) a POSM system configured to produce polypropylene and styrene monomer, and from which the organic stream is generated.

Each of embodiments A, B, C and D may have one or more of the following additional elements: Element 1: wherein the organic stream is a heavy residue formed in the co-production of propylene oxide and styrene. Element 2: wherein the contacting in (a) comprises combining the carbon dioxide with the water to form a $CO_2$-saturated water stream, and contacting the $CO_2$-saturated water stream with the organic stream. Element 3: wherein the contacting in (a) is performed co-currently, counter-currently, or a combination thereof. Element 4: further comprising controlling the concentration of carbon dioxide in the $CO_2$-saturated water stream by controlling the temperature, the pressure, or both. Element 5: wherein the pressure is in the range of from about atmospheric pressure to about 500 psi, from about atmospheric pressure to about 100 psi, from about 10 psi to about 50 psi, or from about 20 psi to about 40 psi. Element 6: wherein the temperature is in the range of from about 5° C. to about 90° C., from about 15° C. to about 70° C., or from about 20° C. to about 60° C. Element 7: wherein the temperature is ambient temperature. Element 8: wherein the temperature is room temperature. Element 9: wherein the contacting in (a) comprises combining the organic stream and the water to form a mixture, and injecting the carbon dioxide as a gas thereinto. Element 10: wherein injecting the carbon dioxide gas further comprises bubbling or sparging the carbon dioxide gas into the mixture. Element 11: wherein the carbon dioxide gas is injected at a flow rate that provides from about 1 wt % to about 90 wt % of the combined mass of the organic and aqueous phases, from about 10 wt % to about 40 wt %, of the combined mass of the organic and aqueous phases or from about 10 wt % to about 25 wt % of the combined mass of the organic and aqueous phases. Element 12: wherein the contacting in (a) is performed at a pressure of greater than or equal to about atmospheric pressure. Element 13: wherein the separating in (b) further comprises separating a gas comprising carbon dioxide, a carrier gas, or both. Element 14: further comprising recycling at least a portion of the separated gas to the contacting of (a). Element 15: wherein (a) and (b) are performed in a single apparatus. Element 16: further comprising: repeating (a) and (b) one or more times on the organic phase; subjecting the organic phase to ion exchange; or both, to obtain an organic phase having a further reduced sodium content. Element 17: comprising subjecting the organic phase to ion exchange, wherein the ion exchange comprises cation exchange. Element 18: the ion exchange is effected with an ion exchange resin comprising sulfonic acid groups. Element 19: wherein the ion exchange is effected with an ion exchange media that is natural or synthetic. Element 20: wherein the ion exchange is effected with an ion exchange resin selected from the group consisting of polymer resins, zeolites, clays, and combinations thereof. Element 21: wherein the further reduced sodium content comprises a sodium content of less than about 100, 50, or 10 ppm sodium. Element 22: wherein the reduced sodium content comprises a sodium content of less than about 250, 150, or 100 ppm sodium. Element 23: wherein the organic stream and the water are present at a volumetric ratio in the range of from about 1:1 to about 10:1, from about 1:1 to about 8:1, or from about 1:1 to about 5:1. Element 24: wherein the contacting of (a), the separating of (b), or both are performed continuously. Element 25: wherein the separating of (b) is performed at a temperature in the range of from about 15° C. to about 85° C., from about 20° C. to about 70° C., or from about 30° C. to about 60° C. Element 26: comprising a two phase system or a three phase system. Element 27: wherein the carbon dioxide is provided as a gas elected from the group consisting of pure carbon dioxide, other gases comprising greater than about 50 volume percent carbon dioxide, and combinations thereof. Element 28: wherein the gas comprising greater than about 50 volume percent carbon dioxide is a flue gas. Element 29: wherein the flue gas comprises greater than about 70 volume percent carbon dioxide. Element 30: wherein at least a portion of the contacting of (a) occurs in a liquid-liquid contactor. Element 31: wherein the liquid-liquid contactor is selected from the group consisting of mixer-decanters, liquid-liquid extractors, mixer-separator devices, and combinations thereof.

While preferred embodiments of the disclosure have been shown and described, modifications thereof can be made by one skilled in the art without departing from the teachings of this disclosure. The embodiments described herein are exemplary only, and are not intended to be limiting. Many variations and modifications of the technology disclosed herein are possible and are within the scope of the disclosure.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the present disclosure. The disclosures of all patents, patent applications, and publications cited herein are hereby incorporated by reference.

What is claimed is:

1. A method comprising:
   (a) conducting a production to produce an effluent comprising propylene oxide and styrene;
   (b) recovering a heavy residue stream from the effluent comprising propylene oxide and styrene;
   (c) contacting water and carbon dioxide with the heavy residue stream to produce a mixture, wherein the mixture comprises an organic phase and an aqueous phase,
   (d) separating the organic phase and the aqueous phase, thereby producing an organic stream and an aqueous stream, whereby sodium is extracted from the organic stream; and
   wherein the aqueous stream comprises an aqueous sodium salt-containing slurry phase from the organic phase comprising a reduced sodium content relative to the organic stream.

2. The method of claim 1, wherein the contacting step comprises combining the carbon dioxide with the water to form a $CO_2$-saturated water stream, and contacting the $CO_2$-saturated water stream with the organic stream.

3. The method of claim 2 further comprising controlling the concentration of carbon dioxide in the $CO_2$-saturated water stream by varying the temperature, the pressure, or both.

4. The method of claim 3, wherein the pressure is in the range of from atmospheric pressure to 500 psi.

5. The method of claim 3, wherein the temperature is in the range of from 5° C. to 90° C.

6. The method of claim 1, wherein the contacting step comprises combining the heavy residue stream and the water to form a mixture, and injecting the carbon dioxide as a gas thereinto.

7. The method of claim 6, wherein the carbon dioxide gas is injected at a flow rate in the range of from 1 wt % to 90 wt % of the combined mass of the organic and aqueous phases.

8. The method of claim 6, wherein the contacting step is performed at a pressure of greater than or equal to atmospheric pressure.

9. The method of claim 1, wherein the separating step further comprises separating a gas comprising carbon dioxide, a carrier gas, or both; recycling at least a portion of the separated gas to the contacting of (a); or both.

10. The method of claim 1, wherein the contacting step and the separating step are performed in a single apparatus.

11. The method of claim 1 further comprising:
repeating the contacting step and the separating step one or more times on the organic phase; subjecting the organic phase to ion exchange; or both, to obtain an organic phase having a further reduced sodium content.

12. The method of claim 11, wherein the further reduced sodium content comprises a sodium content of less than 100 ppm sodium.

13. The method of claim 1, wherein the reduced sodium content comprises a sodium content of less than 250 ppm sodium.

14. The method of claim 1, wherein the organic stream and the water are present at a volumetric ratio in the range of from 1:1 to 10:1.

15. The method of claim 1, wherein the contacting step, the separating step, or both are performed continuously.

16. The method of claim 1, wherein the separating step is performed at a temperature in the range of from 15° C. to 85° C.

17. The method of claim 1, wherein the carbon dioxide is provided by a gas selected from the group consisting of pure carbon dioxide, other gases comprising greater than about 50 volume percent carbon dioxide, and combinations thereof.

18. The method of claim 1, wherein at least a portion of the contacting step occurs in a liquid-liquid contactor.

* * * * *